(12) United States Patent
Regnier et al.

(10) Patent No.: US 8,641,436 B2
(45) Date of Patent: Feb. 4, 2014

(54) ELECTRICAL PLUG HAVING A PLURALITY OF HOUSINGS WITH PODS WELDED TO A PLURALITY OF WIRES AND CONDUCTIVE RINGS

(75) Inventors: Willy Regnier, Longjumeau (FR); Hélène Viatge, Montrouge (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 13/423,030

(22) Filed: Mar. 16, 2012

(65) Prior Publication Data

US 2012/0322318 A1 Dec. 20, 2012

(30) Foreign Application Priority Data

Mar. 16, 2011 (FR) ...................... 11 52166

(51) Int. Cl.
*H01R 27/00* (2006.01)
(52) U.S. Cl.
USPC ........................................................ 439/218
(58) Field of Classification Search
USPC ........................ 439/587, 218, 668
See application file for complete search history.

(56) References Cited

U.S. PATENT DOCUMENTS

| | | | |
|---|---|---|---|
| 6,755,694 B2 * | 6/2004 | Ries et al. ...................... | 439/668 |
| 7,083,474 B1 * | 8/2006 | Fleck et al. .................... | 439/668 |
| 7,108,549 B2 * | 9/2006 | Lyu et al. ....................... | 439/587 |
| 7,175,478 B2 | 2/2007 | Ollivier | |
| 7,287,995 B2 * | 10/2007 | Stein et al. .................... | 439/218 |
| 7,617,006 B2 * | 11/2009 | Metzler et al. ................ | 607/117 |
| 7,641,520 B2 * | 1/2010 | Marino ........................... | 439/668 |
| 2005/0221671 A1 | 10/2005 | Lyu et al. | |
| 2009/0203258 A1 | 8/2009 | Guenther et al. | |

FOREIGN PATENT DOCUMENTS

| | | |
|---|---|---|
| EP | 1641084 A1 | 3/2006 |
| EP | 2090332 A2 | 8/2009 |

OTHER PUBLICATIONS

Foreign Search Report (Annexe Au Rapport De Recherche Preliminaire Relatif A La Demande De Brevet Francais No. FR 1152166 FA 748939), Nov. 2, 2011.

* cited by examiner

*Primary Examiner* — Chandrika Prasad
(74) *Attorney, Agent, or Firm* — Foley & Lardner LLP

(57) ABSTRACT

An electrical connection plug for a multipolar lead of an active implantable medical device. This plug has a cylindrical outer surface including a plurality of annular electrical contact zones axially separated and formed of conductive cylindrical rings (101, 102, 103), the electrical contact zones being alternatively separated by a plurality of intercalary insulating cylindrical zones. The plug includes an insulating monobloc core (200) of a generally cylindrical shape having a plurality of cylindrical side surfaces (213*a*) for coaxial centering, a conductive ring being placed on at least one centering side surface. The central core also includes housings for receiving conductive pods (240) on which connection wires (21, 22) are welded, a pod being welded to a conductive ring.

12 Claims, 6 Drawing Sheets

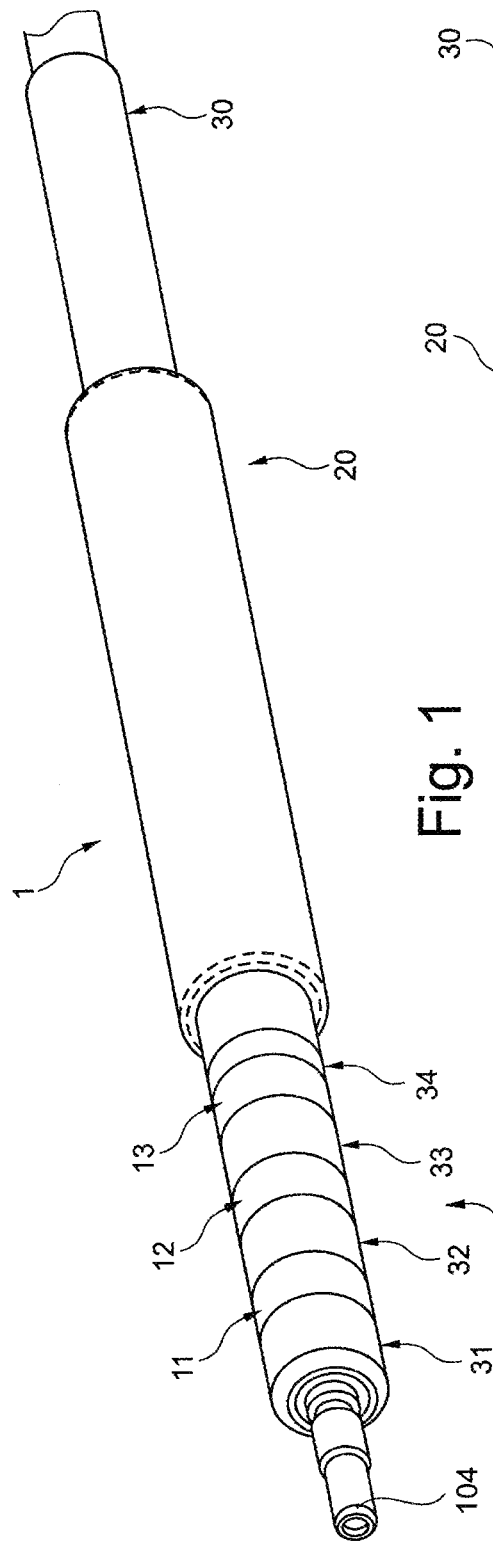
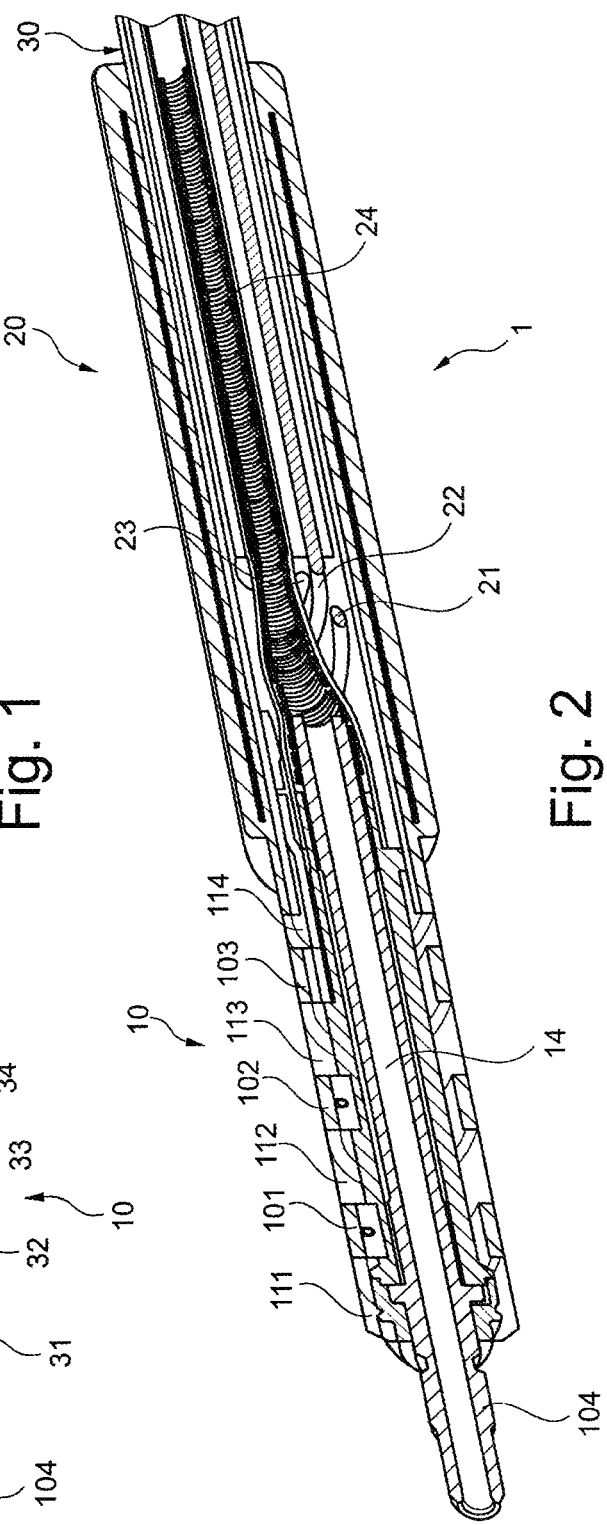
Fig. 1
Fig. 2

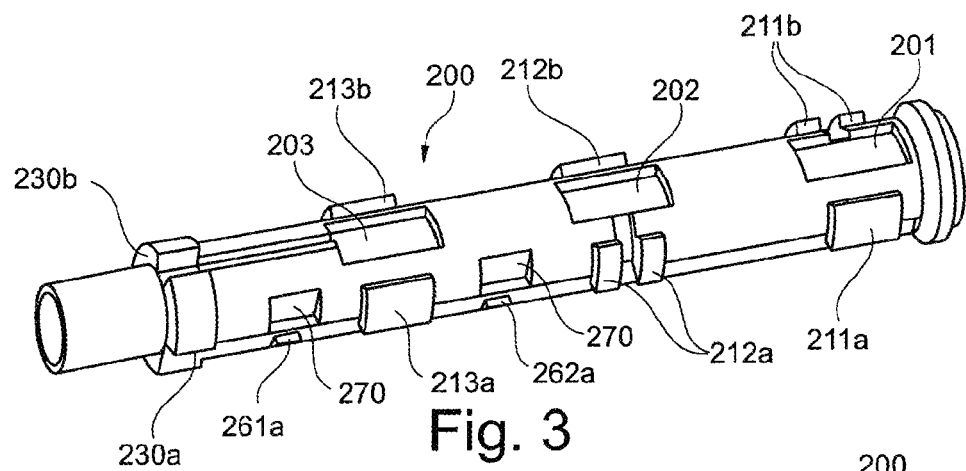
Fig. 3
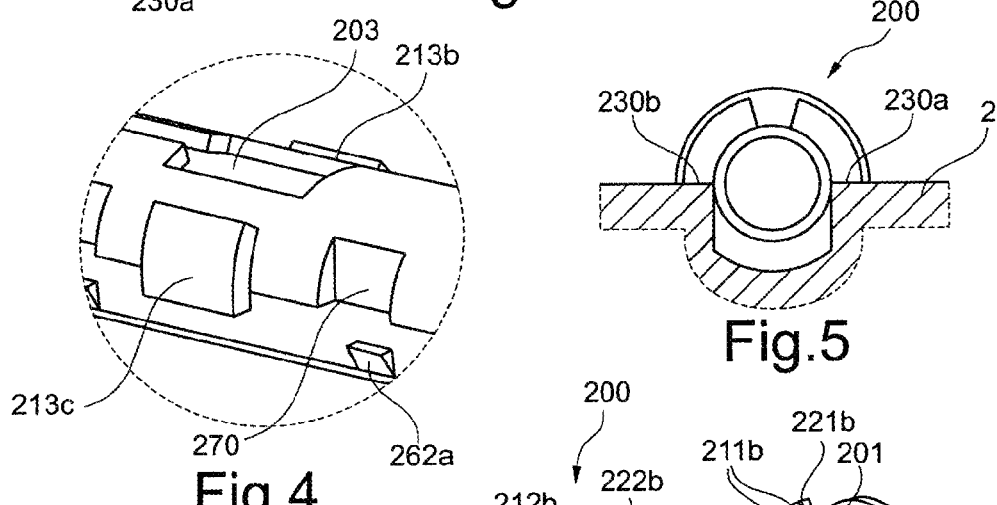
Fig. 4
Fig. 5
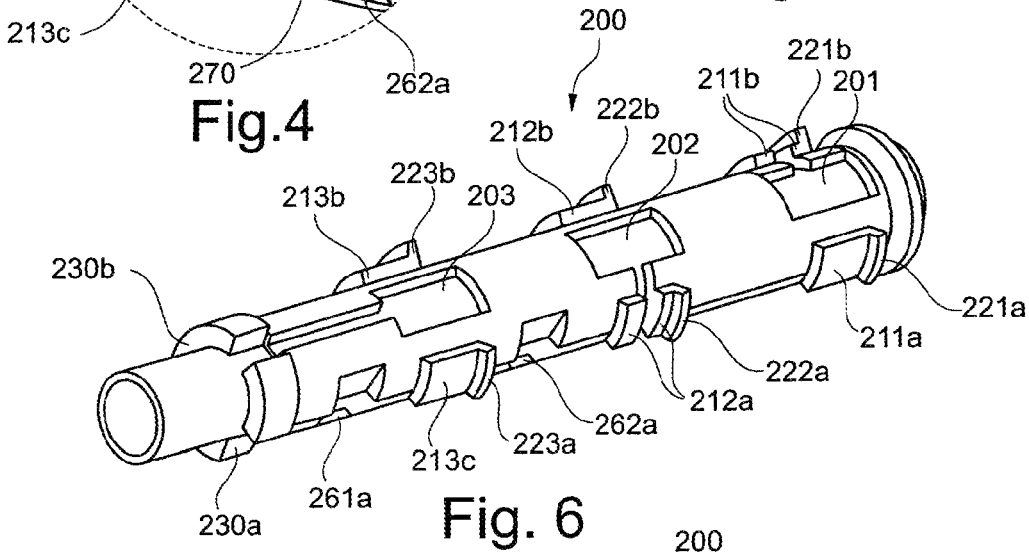
Fig. 6
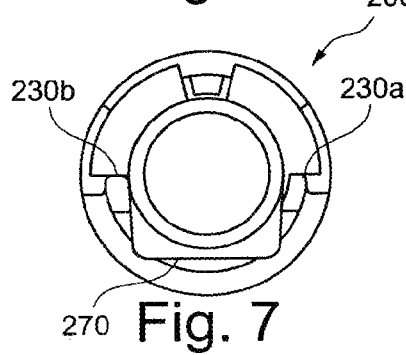
Fig. 7

ELECTRICAL PLUG HAVING A PLURALITY OF HOUSINGS WITH PODS WELDED TO A PLURALITY OF WIRES AND CONDUCTIVE RINGS

The present application claims the benefit of French Application No. 1152166 entitled "Electrical Connection Plug For A Multipolar Lead Of Active Implantable Medical Device" and filed Mar. 16, 2011, which is hereby incorporated by reference in its entirety.

FIELD

The present invention relates to active implantable medical devices as defined by the Jun. 20, 1990 directive 90/395/CEE of the European Community Council, more particularly to devices that continuously monitor the cardiac activity of a patient and deliver if necessary to the heart electrical pulses for stimulation, cardiac resynchronization, cardioversion and/or defibrillation in case of a rhythm disorder detected by the device, and to neurological devices, cochlear implants, drug pumps, and implanted biological sensors. The present invention even more particularly relates to an electrical multipolar connection plug for a lead such as a monobody lead equipped with both stimulation and defibrillation shock electrodes.

BACKGROUND

Active implantable medical devices generally include a housing, which is often called "the generator", that is mechanically and electrically connected to one or more "leads" that have electrodes that in turn come into contact with the tissues to which it is desirable to apply electrical pulses and/or to collect an electrical signal of the patient's myocardium, nerve, or muscle.

Standardized connection systems have been used for years to ensure an interchangeability of the leads and generators produced by different manufacturers. Thus, the standards called "IS-1" and "IS-4" define a number of dimensional and electrical characteristics for the leads to be connected to the generator. For defibrillation or cardioversion leads, wherein electrical stresses are more severe in view of the high energy passing from the generator to the lead, the "DF-1" and "DF-4" standards define the dimensional and electrical characteristics of the connection system.

The complexity of multi-polar leads, which already incorporate specific constraints in terms of the electrical energy associated with delivery of pacing or shock pulses, is enhanced by the development of multisite devices and intracardiac sensors, such as peak endocardial acceleration (PEA) sensors. This complexity leads, in terms of connectivity, to a proliferation of connection plugs, in addition to different standards depending on the plugs.

It is thus desirable to obtain a single plug that is subject to a single standard having a plurality of electrical contacts to simultaneously ensure connections to various terminals of the generator for all applicable energy levels, whether for the collection of depolarization signals, for the application of stimulation pulses or for the delivery of a defibrillation shock. In this context, a single "isodiametric" connection plug, namely a plug having a uniform cylindrical shape, designed to be inserted in a counterpart cavity of the generator, is known.

EP 1641084 A1 and its counterpart U.S. Pat. No. 7,175,478 (both assigned to Sorin CRM S.A.S. previously known as ELA Medical) describes one such isodiametric connection plug with the outer cylindrical surface having a stack of annular electrical contact zones, realized with alternating conductive cylindrical rings and insulating zones, the latter designed to electrically isolate the conductive rings. In addition, each electrical contact in the cavity of the generator must be isolated from the other contacts and from the environment outside the cavity by suitable seals. Originally placed on the lead, these joints are now placed in the cavity because of the fact, more particularly for defibrillation leads, high voltages are applied to the contact elements. It is therefore essential that the connecting pins of the multipolar leads are dimensionally stable over time and comply, with precise tolerances, with the geometric description of the imposed standards. These requirements help ensure that the electrical contact zones and insulating zones coincide with the corresponding zones of the cavities of the generators, when inserting the connector plugs into the cavities, as well as during the useful life of the active implantable medical device.

In this context, two key parameters must be taken into account, namely, on the one hand, the surface state of the electrical contact and insulating zones, and on the other hand, the coaxiality of the electrical contact and insulating zones along the connection plug. These parameters are indeed crucial for the quality of the electrical contact in the generator cavity and for sealing the system.

With these constraints, the difficulty of making a plug connector with a constant diameter along the entire length of the part and with multiple electrical contacts is increased, which in turn raises many manufacturing problems. In addition, the constraint of a small outer diameter (e.g., 3.2 mm according to ISO 27186) limits the design possibilities, so that the impact of complying with tight tolerances that are needed for industrial production can be considerable in terms of time and cost.

In this context, the connection plug described in EP 1641084 A1 and U.S. Pat. No. 7,175,478 mentioned above is not entirely satisfactory, because it does not guarantee a perfect coaxiality of the different zones. Indeed, in this prior art plug, the electrical contact zones and insulating zones are defined by cylindrical elementary parts the axial and angular alignment of which is obtained by longitudinal rods fitted in bores formed in each counterpart section of elementary parts. However, the minimum functional space between the pins and bores to allow stacking of the elementary parts leads to a lack of concentricity of the assembly, detrimental to the electrical contact and sealing of the connection plug inside the generator cavity.

U.S. Patent Publication No. 2005/221671 A1 proposes a plug for electrical connection of a multipolar lead for an active implantable medical device, said plug having a cylindrical outer surface including a plurality of annular electrical contact zones axially distributed and formed of conductive cylindrical rings, the electrical contact zones being alternately separated by a plurality of intercalary insulating cylindrical zones. The plug connector further includes an insulating monobloc core, a piece having a generally cylindrical shape and a plurality of coaxial centering side cylindrical surfaces, with a conductive ring being placed on at least one centering side surface. The desired coaxiality of the conductive rings directly results from the centering side surfaces formed during the manufacture of the monobloc core piece. The fact that there is a unique piece for the central core, so with no functional clearance, ensures the long term stability of the coaxial rings.

However, the described structure requires welding the wire "blind" in a through-hole of the conductive ring, without the possibility of any visual inspection of the weld integrity. The problem of correct positioning of the different rings (i.e., the conductive rings provided with their welded wire and the insulating rings) during the assembly of the plug also remains, while satisfying the constraints of longitudinal alignment and of centering of the rings (namely, for an optimum, and desired perfect, coaxiality of the electrical contact and insulating zones), with a sufficient reproducibility and reliability, without significant increase in production costs and with simple parts and simple manufacturing and control processes, as appropriate for an industrial solution with profitability and efficiency for production in large quantities.

OBJECT AND SUMMARY

To this end, broadly, the present invention is directed to a multipolar lead having a core comprising a plurality of housings receiving a corresponding plurality of intermediary conductive pods on which connection wires are welded, the pods being welded to respective conductive rings.

Advantageously, the intermediate pods have a slot for insertion of the connection wire, aligned in the axis of the core or transverse to the core axis.

In practice, the conductive rings are brought into position on the respective electrical contact zones by sliding each along the central core. To facilitate this operation, the present invention discloses that the side surfaces preferably have a centering longitudinal positioning shoulder for the conductive rings. The shoulders of the side surfaces operate in this way as an abutment for the conductive rings. This in turn provides very good precision in the positioning of the rings.

In one embodiment, to facilitate the introduction of the rings on the core, advantageously the central core has a longitudinal flat for an introduction of the conductive rings on the centering side surfaces by reversible elastic deformation. A slightly oval shape is given to the rings for introduction into the core, by a slight pressure applied to the rings, possibly passing over the positioning shoulders, and axially sliding them into position, then releasing the pressure so that the rings recover their initial annular shape and engage and conform closely to the centering side surfaces.

Preferably, the intermediate insulating areas are formed by insulating rings. In this embodiment, the insulating rings are alternately threaded onto the core with the conductive rings. In an alternative embodiment, the insulating rings can be made by overmolding on a conductive ring. In yet another embodiment, the intermediate insulating zones are preferably made by injection molding of an insulating material. This process concerns filling the spaces created between the conductive rings to make an isodiametric part that especially satisfies the applicable standard, in this embodiment the ISO 27186 requirements.

According to a preferred embodiment, the core is molded of an insulating material such as polyetheretherketone (PEEK) or Tecothane (registered trademark), which materials are commercially available for medical purposes.

Preferably, the cylindrical shape of the core allows a "natural" release, along the axis of opening of the mold, without drawers or spacers. This molding process allows for providing very precise dimensional characteristics on its surfaces, including the centering surfaces and on concentricity. Of course, the same mold can be used to make many parts. This results in excellent reproducibility of the dimensions from one part to another and commercial practicability.

It should be understood, however, that the advantage of the preferred method involving molding does not prevent the core from being manufactured by machining or any other method of producing the isolating parts as would be understood by one of ordinary skill in the art.

Advantageously, the present invention also addresses and resolves an issue which pertains to holding the wires in position for the bonding, which wires extend axially along the central core, from the lead to the electrical contacts of the connection plugs with the generator. In this regards, floating wires can touch each other or touch a conductive ring and are undesirable.

To this end, the present invention preferably provides means for maintaining conductor connection wires along the cylindrical core which are formed on the centering side surfaces to avoid this concern. In particular, the holding means comprises a longitudinal slot formed on the centering side surfaces for applying a connection wire against the cylindrical core. Advantageously, the holding means further comprises at least one second centering side surface intended to hold a connection wire in at least one longitudinal notch.

Thus, the centering side surfaces have a dual function, that of ensuring the proper centering of the conductive rings and that of holding in place the wire for the connection bonding.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is a perspective view of a multipolar lead equipped with a connection plug in accordance with a preferred embodiment of the present invention;

FIG. 2 is a longitudinal section of the lead of FIG. 1;

FIG. 3 is a perspective view of the central core of the connection plug shown in FIGS. 1 and 2;

FIG. 4 is a detail view of the core of FIG. 3;

FIG. 5 is a front view of the central core of the FIG. 3 disposed on a support;

FIG. 6 is a perspective view of one embodiment of the central core of FIG. 3;

FIG. 7 is a front view of an embodiment of the central core of FIG. 3 having a longitudinal flat;

DETAILED DESCRIPTION

Figure 8A:
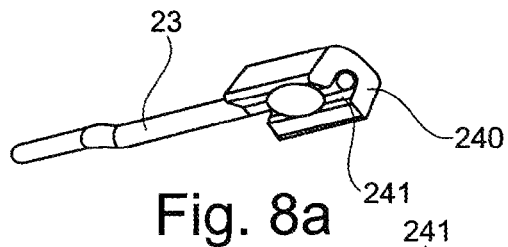
FIGS. 8a and 8b are perspective views of a first method for mounting a connection wire on an intermediary pod.

With reference to FIGS. 1 and 2, the proximal end of a multipolar lead of an implantable medical device, such as a pacemaker, defibrillator or a resynchronizer, is shown. The lead 1 includes a lead body 20 on which various connection conductors extending through a connection plug 10 are arranged in between an electrical pulse generator (not shown) and the poles of the lead 1 placed at the distal end of body 20. In the embodiment illustrated in FIGS. 1 and 2, four connection conductors are represented, including a hollow conductor 24, such as a coiled cable, electrically connected to an axial pin 104 providing an electrical contact with the axial generator and having at its center a lumen communicating with a corresponding lumen 14 formed in the axial pin 104. This allows the introduction of a stylet for the practitioner to guide the lead during implantation in the patient or for the passage of a (conventional) screw fixation system for the lead.

The hollow conductor 24 is housed inside a flexible sheath 30 of insulating material such as silicone, which has excellent fatigue resistance properties. However, to facilitate its introduction into the venous system, the sheath 30 is externally provided with a coating material having a low friction coefficient, for example, polyurethane.

In addition to the hollow conductor 24, the sheath 30 includes, in the non-limiting example illustrated in FIG. 2, three other connection conductors, the wires 21, 22, 23 whose proximal ends are respectively connected to three zones 11, 12, 13 of ring electrical contact axially located along the connection pin 10. As can be seen in FIGS. 1 and 2, the latter is a multipolar cylindrical connection pin, plugged in a single movement in a counterpart cavity of the generator. This method of simultaneous plugging ensures the electrical connection of the various electrodes located at the poles of the lead 1 to the corresponding terminals of the generator. Such a multipolar connection plug is notably described in EP 1641084 A1 and U.S. Pat. No. 7,174,478 mentioned above.

The plug 10 of FIGS. 1 and 2 forms an "isodiametric" assembly, that is to say in which the zones 11, 12, 13 of annular electrical contact and the intercalary isolating zones 31, 32, 33, 34 alternately separating the contact zones exhibit a smooth cylindrical outer surface. In the embodiment illustrated in FIGS. 1 and 2, the zones 11, 12, 13, are made by conductive cylindrical rings 101, 102, 103 which are connected to the wires 21, 22, 23 according to a method described hereafter.

The connection plug 10 is organized around a generally cylindrical hollow monobloc central core 200, an exemplary embodiment of which is shown in FIG. 3. As indicated above, core 200 can advantageously be made by natural molding of an insulating material such as PEEK (polyetheretherketone) or Tecothane (registered trademark). Recesses generically denoted 270 in FIG. 3 are provided on the body of the core 200 to provide a form that is useful to simplify the removal of second retaining side surfaces 262a (see FIGS. 4, 11).

The central core 200 is mainly characterized by the presence of side surfaces 211a, 211b, 212a, 212b, 213a, 213b for coaxial centering, to obtain a very simple and low cost optimum coaxiality of the annular conductive rings 101, 102, 103 when during the assembly of the plug 10, they are placed on the side surfaces. To this end, the curvature of the side surfaces and the inner curvature of the rings must be identical. FIG. 4 is a more detailed view of the side surfaces 213a, 213b.

The electrical connection between the connection wires 21, 22, 23 and the annular conductive rings 101, 102, 103 preferably can be performed as follows. Initially, according to FIGS. 8a, 8b, 9a, 9b, the connection wires 21, 22, 23 are connected to intermediate conductive terminals pods, generically referenced 240, which are disposed within housings 201, 202, 203 provided on the core 200 and which can be seen in greater detail in FIGS. 3, 4, 6, 10.

Pods 240 are preferably made of a biocompatible conductive material, such as stainless steel 316 SS or MP35N. The connection wires 21, 22, 23 are preferably protected by an insulating sheath made of Ethylene TetraFluoroEthylene (ETFE) or PolyTetraTluoroEthylene (PTFE), the wires being then stripped to their end connected to the terminal through intermediary pod 240. Pods 240 can be machined.

Given the position of housings 201, 202, 203 on core 200, that is to say at the location of annular rings 101, 102, 103, the external curvature of pod 240 must be compatible with the inner curvature of the rings.

Figure 9A:
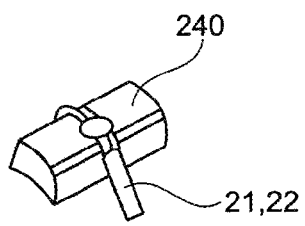
FIGS. 9a and 9b are perspective views of a second method for mounting a connection wire on an intermediary pod.
Figure 8B:
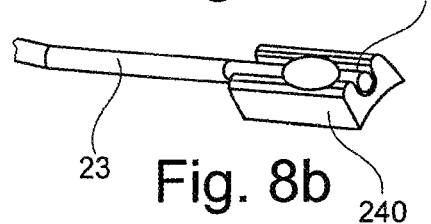
Figure 9B:
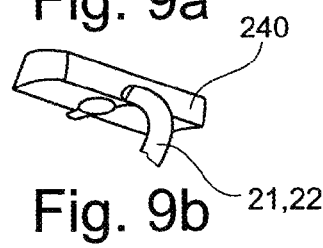
Figure 10:
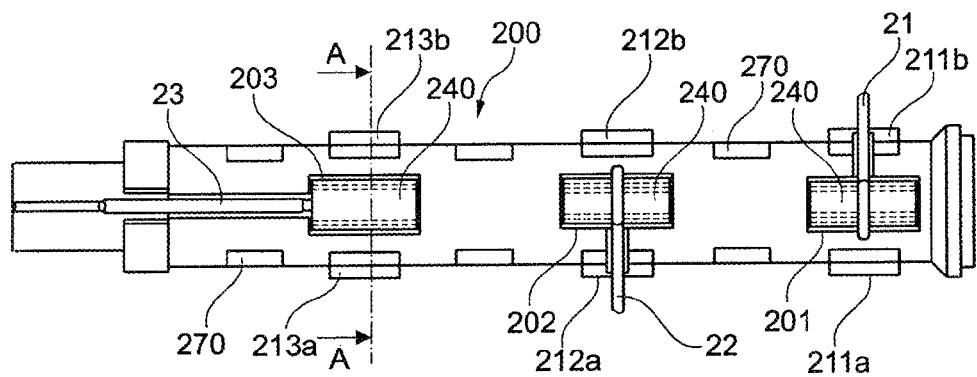
FIG. 10 is a top view of the central core of FIG. 3 with intermediary pods.

Two embodiments of pod 240 are proposed. The first version, as illustrated in FIGS. 8a, 8b, allows directly alignment of connection wire 23 in the axis of core 200. In this case, to allow easier introduction of connection wire 23, intermediary pod 240 has an insertion groove 241. In the second version, as illustrated in FIGS. 9a, 9b, wires 21, 22 are transversely placed, making it necessary to bend them and fold them to realign them in the axis of core 200 and redirect them to body 20 of the lead.

The electrical connection between connection wires 21, 22, 23 points and intermediary pod 240 can be achieved by laser welding, electric welding or any other suitable technology for linking together two metal parts.

Then, pods 240 provided with their respective wires are placed in housings 201, 202, 203. The wires 21, 22 which are transversely coming out of the axis of the core 200 are inserted into slots formed on the side surfaces 212a and 211b and then they are bent and folded so that they extend along the core 200, in parallel to its axis, as shown in FIG. 11.

The assembly operation can be performed under conventional binocular viewing, with the support tooling shown in FIG. 5, wherein the core 200 is placed on a horizontal support on a hollowed plate 2 with two lateral wings 230a, 230b arranged at the end to the core.

Figure 11:
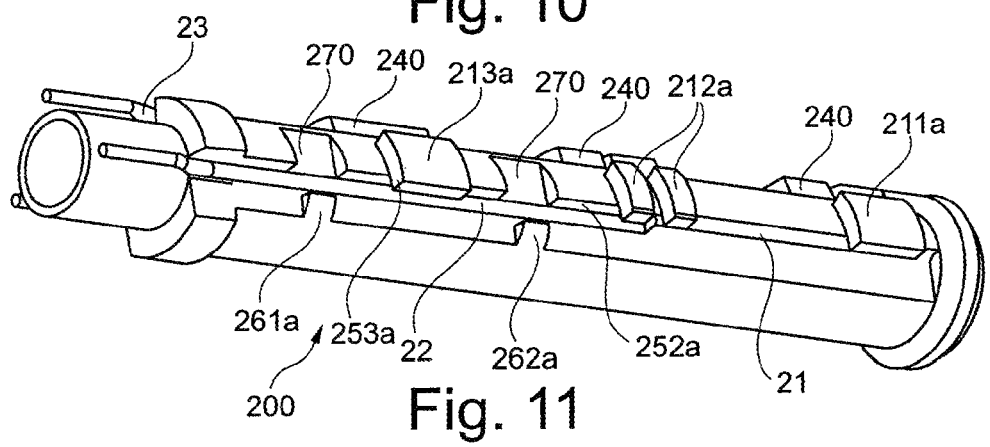
FIG. 11 is a perspective view of the central core of the FIG. 10 showing means for holding the connection wires.

According to an advantageous feature, core 200 is provided with means for maintaining connection points of wires 21, 22 in their position illustrated in FIG. 11, namely against the core and parallel to its axis. These holding means generally include longitudinal notches formed on the centering side surfaces.

Figure 12:
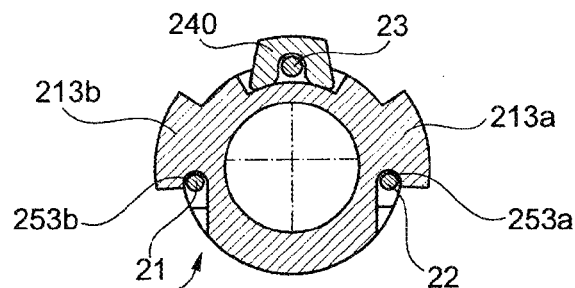
FIG. 12 is a sectional view taken along line AA of FIG. 10.

For example, the section view of FIG. 12 shows longitudinal slots 253a, 253b formed in the centering side surfaces 213a, 213b, these notches being intended to respectively apply and maintain the connection wires 21, 22 against the core 200. As shown in FIG. 11, connection wire 22 is also maintained by longitudinal slot 252a of side surface 212a.

In order to improve the retention position of the connection wires, second centering side surfaces are provided on the core 200 to retain the connection wires 21, 22 in the longitudinal slots once they are introduced there. As illustrated in FIG. 11, for example, the second retaining side surfaces of wire 22 are referenced 261a, 262a. Other side surfaces of this type, not shown in the drawings, are symmetrically present to hold the wire 21 into the corresponding slots.

Figure 13:
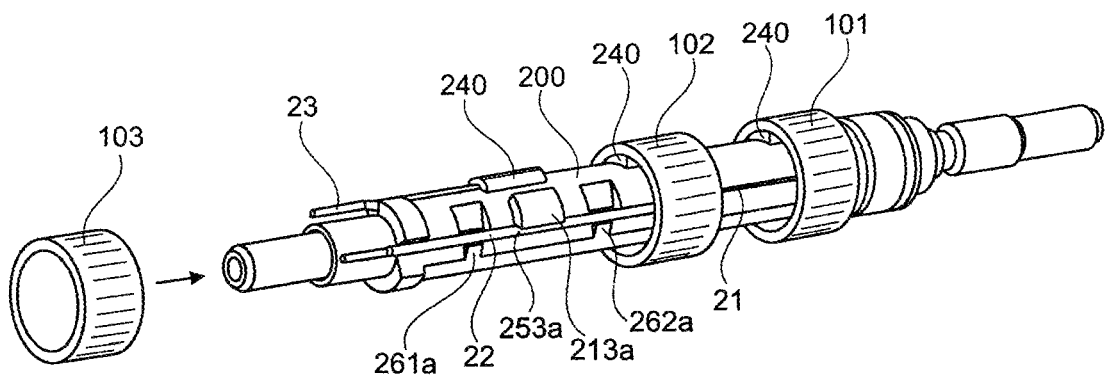
FIG. 13 is a perspective view of a connection plug in accordance with an embodiment of the present invention during assembly of the conductive rings.
Figure 14:
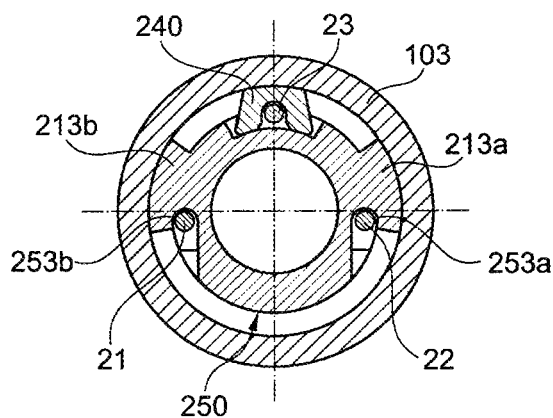
FIG. 14 is a sectional view of FIG. 12 of the connection plug shown in FIG. 13.
Figure 15:
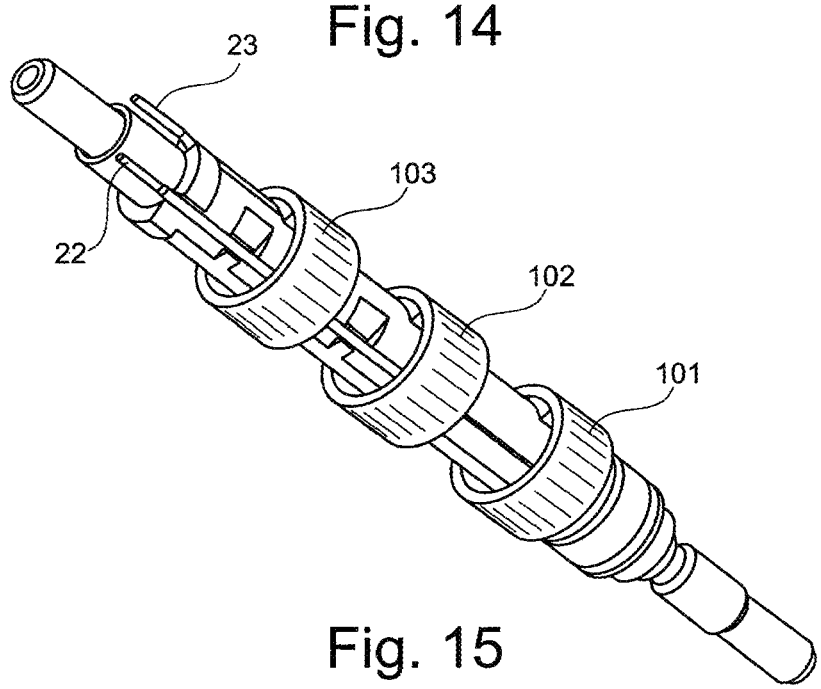
FIG. 15 is a perspective view of a connection plug in accordance with an embodiment of the present invention after assembly of conductive rings.
Figure 16:
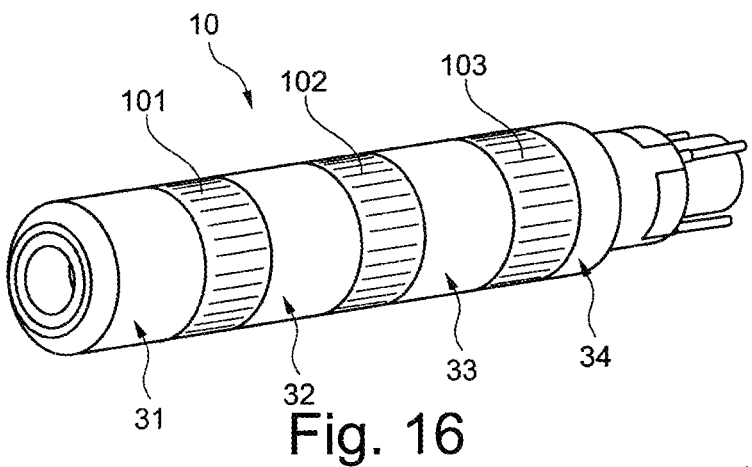
FIG. 16 is a perspective view of the connection plug after an overmolding of the intermediary insulating zones in accordance with one embodiment of the present invention.

According to FIG. 13, conductive annular rings 101, 102, 103 are then put in place by sliding along the axis of core 200 to get them respectively next to pods 240 to which they must be electrically connected. FIG. 14 shows a sectional view of the final disposition of the conductive ring 103 around the core 200. The core 200 equipped with all conductive rings is shown in FIG. 15.

Rings 101, 102, 103 are then welded to intermediate pods 240 by laser welding, electrical welding or any other suitable technology. This can be done ring after ring or on all the three rings placed at once on a positioning tool. It should be understood that the welded connection should not affect the surface finish and cylindricity of the rings. For this, for example, a welding on the side of the ring, tilting the assembly formed by the core 200, conductor wires 21, 22, 23 connected to pods 240 and to rings 101, 102, 103 can be performed. This welding step is preferably a perfectly controlled and inspectable process, made easier by central core 200 which partly plays the role of an internal tool.

The conductive rings have an outer diameter given by the applicable standard, e.g., ISO 27186. Their positioning is critical, as is their coaxiality. As already mentioned, the coaxiality is achieved by centering the side surfaces on which the rings are in support. The longitudinal positioning can be ensured by shoulders 221a, 221b, 222a, 222b, 223a, 223b respectively carried by side surfaces 211a, 211b, 212a, 212b, 213a, 2123b that can be seen in FIG. 6, and against which rings 101, 102, 102 abut.

Figure 21:
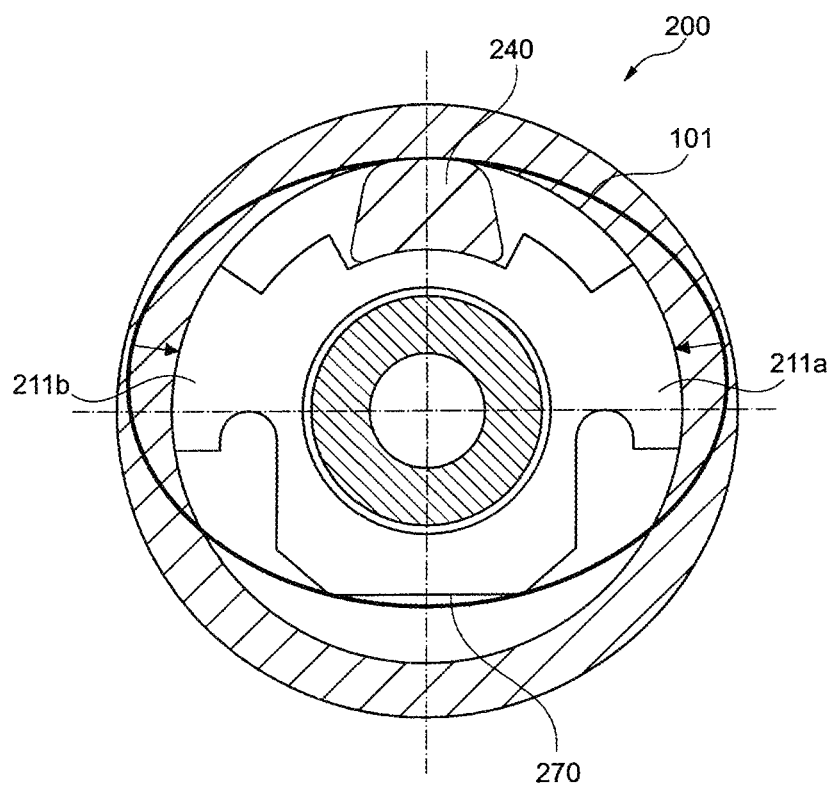
FIG. 21 is a sectional view of the central core of FIG. 7 showing a method for introduction of the conductive rings by elastic deformation.

In this embodiment, it is expected that core 200 has a longitudinal flat 270, shown in FIG. 7, allowing introduction of the conductive rings on the centering side surfaces by reversible elastic deformation. As shown in FIG. 21, a conductive ring, such as ring 101 may according to this method be brought into position by successively crossing shoulders 223a, 223b, and shoulders 222a, 222b.

The final step is to fill the spaces 111, 112, 113, 114 shown in FIG. 2 between rings 101, 102, 103 with an insulating material to achieve the intercalary insulating zones 31, 32, 33, 34 alternately separating the contact zones 11, 12, 13, as shown in FIG. 1. In this operation, it must be ensured that the connection plug 10 is fully isodiametric in accordance with the applicable standard, e.g., ISO 27186, and that it guarantees the tightness of the system, which results, as noted above, in the quality of contact of the plug 10 with the seals arranged in the cavity of the generator receiving the plug.

Figure 17:
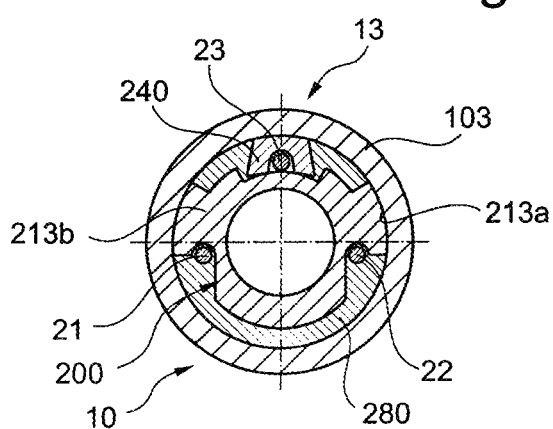
FIG. 17 is a sectional view of the plug of FIG. 16 through a contact zone.
Figure 18:
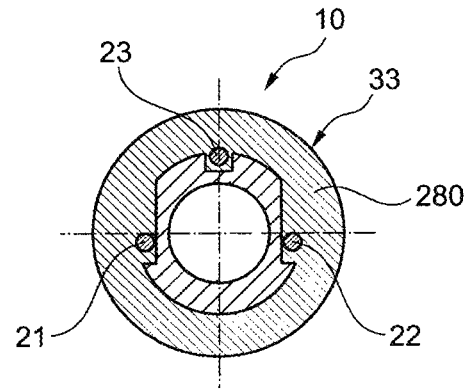
FIG. 18 is a sectional view of the plug of FIG. 16 through an intermediary insulating zone.

Filling spaces 111, 112, 113, 114 can be achieved, for example, by overmolding or injection of glue or plastics, or of another insulating material. FIGS. 17 and 18 respectively show a section of connection plug 10 through electrical contact zone 13 and a section through insulating zone 33 after overmolding with an insulating material 280.

Figure 19:
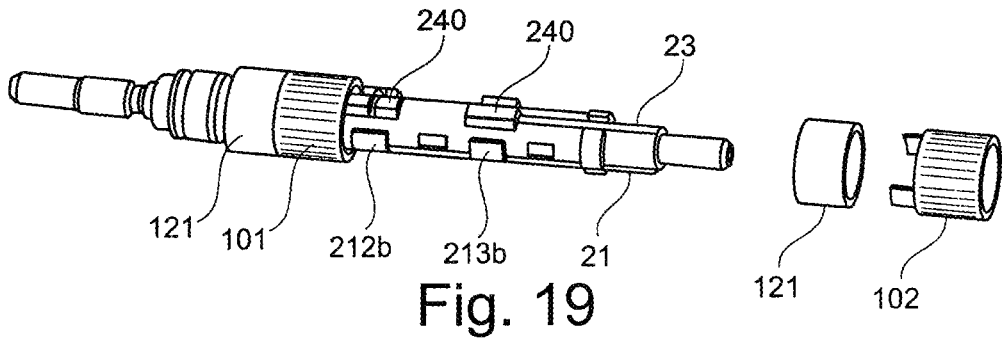
FIG. 19 is a perspective view illustrating an embodiment of the intermediary insulating zones.
Figure 20:
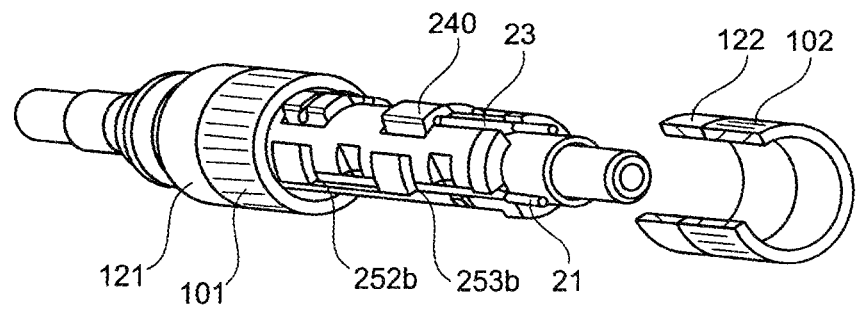
FIG. 20 is a perspective view illustrating another embodiment of the intermediary insulating zones.

According to an alternative embodiment as illustrated in FIG. 19, the isodiameter desired for plug 10 is obtained by providing a stack of insulating rings, such as those referenced 121, 122 in FIG. 20 above, and of conductive rings, the coaxiality of all rings being provided by the centering side surfaces described above, the connection between a conductive ring and a subassembly formed by a connection wire and the corresponding pod being performed before each insertion of an insulating ring.

The second variant of FIG. 20 implements pairs consisting of an insulating ring overmolded onto a conductive ring, such as pairs ring 121/ring 101 and ring 122/ring 102, each pair being connected by the conductive ring to a subassembly connection wire/pod before the introduction of a new pair.

It should be understood by a person of ordinary skill in the art that the present invention not only greatly simplifies the assembly of a multipolar lead connection plug, but it also allows a visual inspection at each stage of assembly. The operator thus has better control at each stage of the process.

In addition, the connection plug of the present invention can either be performed directly on an existing lead body or subsequently be connected to the lead. This allows the possibility to outsource the manufacturing of the plug and to adapt it to any lead body.

One skilled in the art will appreciate that the present invention can be practiced by other than the embodiments described herein, which are provided for purposes of illustration and not of limitation.

The invention claimed is:

1. A plug for electrical connection to a multipolar lead for an active implantable medical device, the plug having a cylindrical outer surface including a plurality of electrical contact zones formed of a plurality of conductive cylindrical rings, said electrical contact zones being alternately separated by a plurality of insulating cylindrical zones, said plug comprising an insulating monobloc central core having a generally cylindrical shape and a plurality of cylindrical side surfaces for coaxial centering of the conductive cylindrical rings about the central core, one of the conductive cylindrical rings being placed on at least one cylindrical side surface, and wherein the central core comprises a plurality of housings for receiving a corresponding plurality of conductive pods on which connection wires are welded, each pod being respectively welded to a conductive ring.

2. The plug of claim 1, wherein each said conductive pod further comprises a slot for insertion of one of the connection wires, aligned in the core axis or transverse to this axis.

3. The plug of claim 1, wherein the centering side surfaces have a shoulder for longitudinal positioning of the conductive rings.

4. The plug of claim 3, wherein the central core has a longitudinal flat adapted for an introduction of the conductive rings on the centering side surfaces by reversible elastic deformation.

5. The plug of claim 1, wherein the insulating cylindrical zones are intercalary and are formed by insulating rings.

6. The plug of claim 5, wherein an insulating ring is overmolded on a conductive ring.

7. The plug of claim 1, wherein the core is molded of an insulating material.

8. The plug of claim 1, comprising means for holding the connection wires along the cylindrical central core, formed on the centering side surfaces.

9. The plug of claim 8, wherein the holding means comprise a longitudinal slot formed in the centering side surfaces and for applying a connection wire against the cylindrical core.

10. The plug of claim 9, wherein the holding means further comprise at least one second centering side surface for retaining a connection wire in at least one longitudinal groove.

11. The plug of claim 1, wherein the intercalary insulating zones are made by overmolding an insulating material.

12. The plug of claim 1, wherein the intercalary insulating zones are made by injection of an insulating material.

* * * * *